United States Patent [19]

Azhar et al.

[11] Patent Number: 5,260,195
[45] Date of Patent: Nov. 9, 1993

[54] NONAQUEOUS POLYMERIC REAGENT COMPOSITIONS AND APPLICATIONS THEREOF

[75] Inventors: Abol F. Azhar, Fishers; Arthur M. Usmani; Anthony D. Burke, both of Indianapolis; Jill DuBois-Bousamra, Fishers; Eric R. Diebold, Fishers; Myron C. Rapkin, Indianapolis; all of Ind. Mark T. Skarstedt, Franklinville, N.J.

[73] Assignee: Boehringer Mannheim Corporation, Indianapolis, Ind.

[21] Appl. No.: 638,263

[22] Filed: Jan. 3, 1991

[51] Int. Cl.$^5$ .................................. C12Q 1/26
[52] U.S. Cl. ........................ 435/25; 435/28; 435/188; 435/805; 436/166; 436/518; 436/524; 422/56
[58] Field of Search ............. 435/188, 805, 25, 28; 436/166, 518, 524; 422/56

[56] References Cited

U.S. PATENT DOCUMENTS 4,868,106 9/1989 Ito et al. .......................... 435/188

Primary Examiner—Ronald W. Griffin
Assistant Examiner—Pamela S. Webber
Attorney, Agent, or Firm—Marilyn L. Amick; Max J. Kenemore; D. Michael Young

[57] ABSTRACT

Non-aqueous, polymeric reagent film compositions for use with analytical test devices of the dry chemistry type are described. The film compositions are prepared from an organic solution of a copolymer formed by interaction of at least two monomers wherein
(a) the first monomer is a hydroxylated acrylate of the general formula

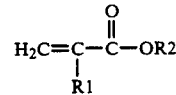

where R1 is hydrogen or, more preferably, methyl, and R2 is a hydroxyalkyl group having from 1 to 5 carbon atoms, and
(b) the second monomer is a neutral acrylate of the general formula

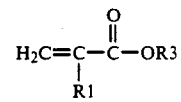

where R1 is hydrogen or, more preferably, methyl, and R3 is a substituted or unsubstituted alkyl group having from 1 to 8 carbon atoms.

Preferably, a third monomer is also included which is an amine-containing acrylate of the general formula

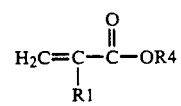

where R1 is hydrogen or, more preferably, methyl, and R4 is a substituted or unsubstituted aminoalkyl or glycidyl group having from 1 to 5 carbon atoms or a surfactant polyethylene glycol group having from 10 to 30 carbon atoms. The film further comprises at least one enzyme in powder form dispersed therein and, optionally, a chromogenic indicator. The film composition is especially useful for determining components in body fluids, for example, for detecting glucose in whole blood, by rapid techniques.

42 Claims, 8 Drawing Sheets

NONAQUEOUS POLYMERIC REAGENT COMPOSITIONS AND APPLICATIONS THEREOF

FIELD OF THE INVENTION

The present invention relates to the field of analytical chemistry, and particularly to that area concerned with the measurement of specific components in biological fluids by dry chemistry methods.

BACKGROUND OF THE INVENTION

The use of dry chemistry techniques in the measurement of specific analytes in biological fluids such as urine and blood has attained prime importance. Among other advantages dry chemistry, or solid phase methods, permit rapid analysis by relatively unskilled personnel, require no reagent preparation, and provide economy of both reagents and sample thus making them ideally suited for patient self-testing, among other uses. In solid phase chemistry, reagents are present in dry form, most frequently in an impregnated matrix. Further, the reagents are normally unitized, i.e., the reagents for each individual test are used and disposed of as a single entity. One convenient and popular form is that of a test strip in which the reagent matrix is affixed to a carrier that supports the reaction area and can also serve as a handle. When the liquid sample, typically blood or urine, which contains the analyte of interest is brought into contact with the test area, the reagents located therein are immediately activated and produce a reaction or sequence of reactions, resulting usually in the formation of a color which can be compared by visual means to a standard color chart or measured more precisely by an instrument such as a reflectance photometer.

One test which is exemplary of the type of assay performable with dry chemistry test devices is the determination of blood glucose, which is important, inter alia, in monitoring diabetic and hypoglycemic patients. A typical test strip, for example, contains the enzymes glucose oxidase and a peroxidase, as well as an indicator such as 3,3',5,5'-tetramethylbenzidine, also referred to as "TMB". If glucose is present in the sample, it reacts with oxygen in the presence of glucose oxidase to form gluconic acid and hydrogen peroxide. The peroxide, in turn, reacts with the TMB in the presence of the peroxidase, oxidizing the TMB. In reduced form, TMB, is colorless; however, when it is oxidized, TMB is blue, red or purple, depending upon the charge transfer complex formed. Thus, one can determine if glucose is present, and in what quantity, by observing the formation of color. This reaction system is analyte specific, because hydrogen peroxide is not a normal component of the sample, and it only forms when the glucose-specific enzyme, glucose oxidase, acts on its substrate.

In its simplest form, a test device of the type used in dry chemistry analyses of the type monitored by diffuse reflectance methods comprises three functional zones or layers. The first, which plays no actual part in the assay, is a support or carrier layer. This layer is inert, impervious to liquids, and is generally constructed from rigid materials such as thermoplastic films. It may be transparent or opaque, depending upon the side through which the reaction is to be observed. A second, reflective layer, which can be a distinctly defined layer or may be incorporated with the carrier material, the reagent layer, or both, may be employed to aid in reading the detectable signal when it forms. This is especially helpful in systems which use a reflected light detector. The reflective layer contains some material which reflects light not absorbed by the detectable signal generator and generally takes the form of a coating, foam, membrane, paper, or metal foil which is reflective. Substances useful for this purpose include pigments such as titanium dioxide, zirconium dioxide, zinc oxide and barium sulfate.

The third functional layer, which can be generally referred to as the reagent layer, contains the reactive ingredients which cause formation of the detectable signal. It is this layer which is actually observed or measured to determine the analyte. Various enzymes, substrates, receptors, and binding partners can be incorporated in this layer, such as labeled antibodies, indicator molecules, fluorescent agents, capping or quenching agents, and so forth.

The sample for analysis is commonly applied by dropping from above the reagent layer, whereupon it makes contact with a spreading or metering layer which is positioned over the reagent layer. In the case of a whole blood sample, the spreading layer will serve also to separate the highly colored red cells from the plasma, which would otherwise interfere in the reaction. The plasma soaks or diffuses into the reagent matrix where the reactions occur. In most types of these soak-through devices, the residual blood sample and cells must be wiped or rinsed from the surface of the test area in order to measure color formation. Alternatively, color may be measured from the bottom of the reaction area provided that, of course, the support upon which the reation matrix rests is formed from a clear, transparent material. A second type of analytical device functions by a relatively horizontal, or parallel, rather than vertical sample flow whereby the sample moves across the top of the reaction area, such as by capillary action, gravity or other forces. As the sample travels over the surface of the reaction area carrying red blood cells and other cellular elements with it, the plasma moves into the reagent layer itself, where it reacts to form a detectable moiety.

Two distinct approaches have been used to construct the zone or layer containing the reagents for the assay. The first approach involves the use of a paper, e.g., cellulose, or synthetic fiber matrix which has been saturated with solutions containing the assay reagents and then dried. In the second approach, the reagent layer is constructed by casting a porous film containing all the required assay components. In the case of constituents which require segregation before use, the reagents may be deposited in several film layers, so that the reagent layer created thereby is actually constructed of multiple film layers, each of which contains a portion of the assay components required. Typically, membranes which separate or trap cellular components from the blood are also used. The quantities of reagents made available during analysis are controlled by their concentration in the casting medium, the thickness of the cast film and their solubility in the sample solvent.

A primary advantage of these films is the high degree of uniformity of the reagent layer. With the use of reagent films and of reflectance photometry, it is now possible to achieve measurement results with dry chemistry strips of the same precision and accuracy as with wet chemistry methods. In the case of these test strips, there is involved mixing a solution or suspension of the reagents and applying the mix to a test strip, followed by evaporation of the liquid. An aqueous solution, or a solution containing a dispersed polymeric binder, is typically employed. These aqueous solution-based systems are problematic for several important reasons. First, many important substances, including TMB and other indicators, are insoluble in water. This, taken with other problems of hydrolytic stability of the reagents and compatibility of the reagents, renders many substances unsuitable for use in test strip devices. Also, if enzymes and substrates, for instance, are mixed in a solution, they will react prior to application of the analyte, with resulting failure of the system. As was pointed out, the liquid phase, such as water, has to be removed from these systems, and this must be done at elevated temperatures to remove all the moisture. Generally, the parameters used for evaporation are 55° C. or higher for a minimum of 20 to 30 minutes, which conditions are sufficient to cause some damage to most enzymatic systems. Thus there is a pressing need to develop techniques in which water is eliminated.

RELATED ART

Illustrative of the art with respect to applications of reagent film layers in dry chemistry devices is Arai et al. U.S. Pat. No. 4,786,595 issued Nov. 22, 1988, (hereinafter Arai) which describes problems in test strips where a diazonium indicator is incorporated into a layer containing polymeric polycarboxylic acids. The solution to the problem taught by Arai is the use of a polycarboxylic acid derivative binder created by esterifying the polycarboxylic acid with a nonionic surface active agent. Preferred polycarboxylic acids are methyl vinyl ether-maleic acid copolymer (50/50), styrene-maleic acid copolymer (50/50), and maleic acid-butyl acrylate copolymer (50/50). There is no specific limitation on the nonionic surface active agent other than it must, of course, contain a hydroxyl group. Arai also describes, at column 11, line 4 et seq., a coupler substrate layer (positioned over the color reaction layer) prepared by dissolving or dispersing a non-diffusive, colorless coupler substrate in a binder solution containing one or more polymers. A variety of hydrophilic binders are taught to be suitable including natural polymers such as gelatin, agarose, sodium alginate and carboxymethyl cellulose, and hydrophilic synthetic polymers such as polyacrylamide, poly(vinyl alcohol), poly(vinylpyrrolidone), poly(sodium acrylate), poly(2-hydroxyethyl methacrylate), acrylic acid copolymers and maleic acid copolymers. Specific exemplification of a polycarboxylic acid derivative binder and a non-esterified binder in an analytical element for measuring cholesterol is given at column 24, line 59 et seq. Peroxidase is incorporated in the aqueous color reaction layer, and cholesterol oxidase and cholesterol esterase are incorporated in the aqueous diffusion-preventive layer using known solution techniques.

Koyama et al. U.S. Pat. No. 4,576,793 issued Mar. 18, 1986, (hereinafter Koyama) describes an analytical element comprising a support, a reagent layer, and a porous spreading layer wherein at least one layer contains 5% or more by weight of a polymer formed by (a) a copolymerizable ethylenically unsaturated acid with (b) a copolymerizable ethylenically unsaturated monomer. The copolymerizable ethylenically unsaturated acid should be contained in an amount of 5% by weight or more of the polymer, preferably 25% or more, and most preferably 45% or more. It is taught, at column 3, line 68 et seq., that "with a content less than 5% by weight, no sufficient effect as (sic.) the analytical element of this invention can be exhibited." The polymer, it is taught, acts as an acid and as a buffering agent. Indeed, in the examples given, assays for bilirubin and urea are taught, both of which require highly acidic reaction conditions. Both of the aforementioned examples incorporate a chromogenic substance in the polymer-containing reagent layer but no enzyme. Koyama mentions incorporation of enzymes into the reagent layer at column 10, lines 26-32; however, specific exemplification is not given, and enzymatic reactions are not generally useful at the low pHs taught.

Okaniwa et al. U.S. Pat. No. 4,427,632 issued Jan. 24, 1984 (hereinafter Okaniwa) teaches the use of a hydrophobic developing layer of a fibrous structure formed by coating a reagent layer with a dispersion comprising a macromolecular polymer having reactive groups and a fibrous material. In use for determining the presence of a component in a liquid sample, the component permeates through the developing layer toward the reagent layer. The polymer is formed from monomers having reactive groups, e.g., carboxyl, amino, methoxy and hydroxyl, and other monomers such as styrenes, nitriles and crosslinking monomers. In the exemplary polymer compounds listed at column 6, lines 15-65 and in column 7, lines 5-24, one notes that nearly all are polystyrenes. Okaniwa describes an assay device for glucose in which a reagent layer containing enzymes and indicator in a gelatin matrix is deposited on a transparent support, and a copolymer layer comprised of styrene and glycidyl methacrylate in the weight ratio of 90/10 is deposited over the reagent layer.

Japanese Patent Disclosure 209995, 1983 (Omoto et al., hereinafter Omoto) describes a method for manufacturing test pieces for examination of body fluids wherein the testing zone is established on a substrate by a printing method using an ink composition consisting of an enzyme, an indicator, a binding agent, and additives dispersed in a nonaqueous solution and mixed. More specifically, Omoto teaches a printing ink composition for detecting the presence of glucose in urine by a qualitative method. The ink comprises freeze-dried enzymes glucose oxidase and peroxidase, o-toluidine, a surfactant, an isobutylene/maleic anhydride copolymer, and a majority of kaolin (about 50% of the dry weight of the composition). The binding agent taught is dissolved in an n-butanol solvent, and following printing onto a substrate, the ink mixture is dried at 80° C. for 1 hour. It must be expected that exposure of the composition to such extreme conditions has a substantial deleterious effect on the enzymes contained therein. The kaolin, or other fine particles taught such as silica clay, calcium carbonate, aluminum silicate, glass, or cellulose are added as water absorbent carriers due to the fact that the polymer composition taught is not sufficiently hydrophilic. The range of polymers taught by Omoto is very broad and includes synthetic polymers such as polyacrylates, polyphenylacetals, polymethacrylates, polyacrylamides, polyurethanes, polyvinyl chlorides, polystyrenes, polymers composed of maleic acid and other ingredients, polyvinyl acetates, polyvinyl alcohols, polyvinyl pyrrolidones, etc.; semisynthetic polymers such as methyl cellulose, ethyl cellulose, propyl cellulose, and other cellulose derivatives, plus starch ethers, etc.; and natural polymers such as starch, casein, polysaccharides, etc. What is taught to be preferred, however, are maleic acid type copolymers containing maleic acid as an ingredient, such as isobutylene-maleic anhydride copolymer, styrene-maleic acid copolymer, etc. Such teachings thus suggest that the polymer and resulting ink composition results in an anionic reaction medium, one that would be unworkable with blood samples with their charged cellular components, and certainly unworkable with the cationic surfactants taught to be useful in the mixture. Such teaching of such a broad range of useful polymers further suggests that little consideration need be given to the properties likely to be imparted by a particular polymer upon the ink mixture, presumably, in part, because the polymer binder comprises only 20% of the total solution (about 30% of the dry weight). As a nonaqueous solvent for the binding agent, Omoto teaches that one can choose at will from among organic solvents including alcohols, ketones, aromatics, various esters, hydrocarbons, etc.

Pierce et al. U.S. Pat. No. 4,258,001 issued Mar. 24, 1981 (hereinafter Pierce) describes a particulate structure for the transport or analysis of liquids which contain high molecular weight, complex molecules and cells. The particulate structure is composed of organopolymeric particles impermeable and non-swellable in the liquid under analysis, and the particles are held together by an organic polymeric adhesive that is different from that of the particles and which bonds the particles into a coherent, three-dimensional lattice which contains an extensive, interconnected void volume. The reagents for the assay can be present in the matrix of the particulate structure, affixed to the surface of the particles or located in a separate zone of the element in fluid contact with the particles. A wide range of homopolymers and copolymers useful for preparation of the particles is disclosed beginning at column 11, line 14. Included are polymerizable amino-substituent-free styrene monomers, acrylic esters, methacrylic esters, ethylenically unsaturated carboxylic acids, ethylenically unsaturated nitriles, amine-substituted styrenes, monomers containing a crosslinkable group, tertiary aminoalkyl acrylate or methacrylate monomers, N-heterocyclic vinyl monomers, and acrylamide or methacrylamide monomers. Hydroxyl-containing monomers are not taught. At column 37, line 40 through column 38, line 17, Pierce teaches the use of these polymeric bead structures in an element for the qualitative determination of glucose in blood wherein the enzymes glucose oxidase and peroxidase are immobilized onto the beads using a slurry mixture prior to preparation of the coated analysis element.

Levy et al. U.S Pat. No. 4,147,764 issued Apr. 3, 1979 (hereinafter Levy) teaches solid hydrogel matrices having particulate sorbents, e.g., activated carbon, entrapped therein. The preferred monomers for preparing the hydrophilic polymers are hydroxyalkyl acrylates and hydroxyalkyl methacrylates, but these can be replaced in whole or in part by vinyl pyrrolidone, acrylamide, N,N-dimethylacrylamide, and others. Levy teaches that these monomers usually form water soluble polymers, and thus they require the presence of sufficient cross-linking agent to render the final product insoluble in water or organic solvents. Other ethylenically unsaturated monomers can be used as comonomers in conjunction with the aforementioned monomers to prepare the matrices, including acrylonitriles, the alkenyl alkanoates, the alkyl 2-alkenoates, and the alkoxyalkyl 2-alkenoates. In use, the product is a solid tablet that is dropped into an aqueous reaction mixture containing a serum sample and radioactive labelled tracer. The tablet's function is to absorb the tracer-bound antigen.

Steckler U.S. Pat. No. 4,060,678 granted Nov. 29, 1977 teaches cationic hydrogels containing basic groups in their molecular structure. These hydrogels are three-dimensional polymer networks obtained by simultaneous polymerization and crosslinking of a mixture of (a) hydroxyalkyl acrylate or methacrylate, (b) a cationic monomer, and (c) a cross-linking agent. There may also be present (d) one or more other monomers, usually an acrylic monomer, which is copolymerizable with (a), (b) and (c). These cationic hydrogels are taught to be useful for combining, by reaction or complexing, with materials having an opposite charge such as acidic or anionic agricultural chemicals, pharmaceuticals, cosmetics, enzymes, flavors, and the like, both to recover such materials from an aqueous medium, for purifying water containing them, and for the preparation of a complex or combination of the hydrogel with such materials from which the material may be slowly or controllably released. At column 12, lines 62–64, Steckler teaches solution dispersion of these materials in preparation of the hydrogel complexes "by immersing or washing the cationic hydrogels in an aqeous (sic.) solution or suspension of an anionic material which it is desired to combine or complex therewith."

SUMMARY OF THE INVENTION

Accordingly, it is an object of this invention to provide a stable reagent film composition which is useful in determining an analyte in a sample and which contains a nonaqueous copolymer, an indicator and at least one enzyme.

It is a further object to provide an analytical test apparatus which is useful for determining an analyte and which comprises the above composition.

It is yet a further object of the invention to provide a method for the determination of an analyte in a sample using the above composition and apparatus.

It is still another object to provide a method for preparing the above composition and apparatus.

The invention comprises a stable copolymer film which contains analytical reagents, such as enzymes, dispersed therein, and which is used either alone, or as part of a diagnostic test apparatus for detecting an analyte in a fluid sample, such as a biological fluid such as blood. By choosing a particular combination of acrylic monomers and a particular combination of nonaqueous solvents, a polymeric film has been developed which permits the incorporation of reagents such as enzymes in dry form without loss of activity. Generally, test strip films require the enzyme to be introduced in solution form, followed by drying. Such processes, however, require elevated temperatures to dry the film, which leads to a certain degree of inactivation of the enzyme reagent. Water solubilization of enzymes leads to certain problems as well, including hydrolysis and additional catalytic deterioration of the enzyme. On the other hand, when dry enzyme powders are used, the reagent is dispersed in the film, rather than adsorbed. This difference means that the film can be nonionic, i.e., of neutral charge. When enzymes are adsorbed onto polymers, it is accomplished via interaction of a charged polymer (cationic) with charged amino acids, which are a part of the enzyme (anionic). A further advantage with respect to the present invention is that many indicators which are either insoluble or only sparingly soluble in water can now be freely used without additional procedural steps, and, moreover, reagents known to be incompatible, unstable, or reactive when contained together in the same reagent mixture, e.g., enzymes and indicators, may now coexist in the same reagent layer. The present invention further comprises a method for preparing the film of the invention and an analytical test device comprising a support upon which the polymeric film of the invention is coated.

The nonaqueous film composition comprises a copolymer formed by the combination of at least two monomers wherein (a) the first monomer is a hydroxylated acrylate of the general formula

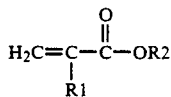

where R1 is hydrogen or, more preferably, methyl, and R2 is a hydroxyalkyl group having from 1 to 5 carbon atoms, and (b) the second monomer is a neutral acrylate of the general formula

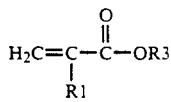

where R1 is hydrogen or, more preferably, methyl, and R3 is a substituted or unsubstituted alkyl group having from 1 to 8 carbon atoms.

Preferably, a third monomer is also included which is an acrylate of the general formula

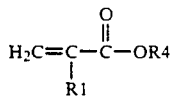

where R1 is hydrogen or, more preferably, methyl, and R4 is hydrogen, an aminoalkyl or glycidyl group having from 1 to 5 carbon atoms, or a surfactant polyethylene glycol group having from 10 to 30 carbon atoms.

The film further comprises at least one enzyme dispersed therein and, optionally, a chromogenic indicator.

DETAILED DESCRIPTION OF PREFERRED EMBODIMENTS

Figure 1:
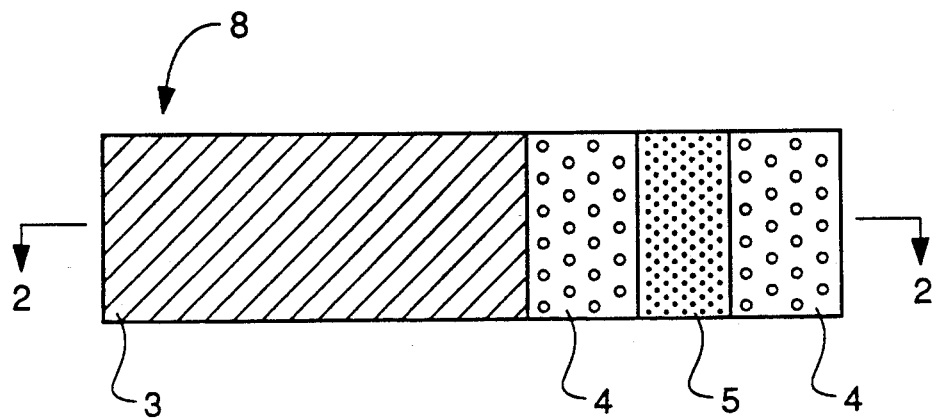
FIG. 1 is a top view illustrating a typical structure of an embodiment of an analytical test apparatus which incorporates the polymeric reagent film composition of the present invention.

An especially preferred embodiment uses a copolymer formed from a mixture of hydroxyethyl methacrylate (HEMA, monomer i), butyl methacrylate (BMA, monomer ii), and dimethylaminoethyl methacrylate (DMAEMA, monomer iii), in percent ratios of 65, 33 and 2, respectively. Monomers i, ii, and iii are then joined by one or more dry enzyme powders dispersed therein, a chromogenic indicator, and optional additional ingredients such as surfactants, ranging compounds, dyes, buffers and viscosity modifiers. The copolymer is prepared under particular conditions including initiators and solvents which result in a nonionic, clear polymeric product.

The monomers are selected so as to impart particular desirable properties to the resulting polymeric film. HEMA, for example, or other hydroxy group containing acrylate (monomer i) is added in a major proportion to impart high levels of hydrophilicity to the film, thus allowing intimate contact with an aqueous sample. Furthermore, it may also have some enzyme stabilizing effects. A neutral acrylic monomer, for example BMA (monomer ii) is added for hardness and flexibility, while an amino-containing monomer, for example DMAEMA (monomer iii), renders the copolymer produced more compatible with enzymes.

Other suitable monomers which may be used instead of HEMA for monomer i include hydroxypropyl methacrylate, hydroxyethyl acrylate, and hydroxypropyl acrylate. A mixture of the aforementioned monomers may also be used. The optimal amount of monomer i is about 50 to 70 percent by weight of the polymer composition, preferably about 65 percent, but may range from 10 to 70 percent. Unsaturated polyesters (based on ethylene glycol, other glycols, phthalic anhydride, maleic anhydride) with HEMA may also be used instead of hydroxylated acrylic polymers.

Other suitable monomers which may be used instead of BMA for monomer ii include methyl acrylate, methyl methacrylate, ethyl acrylate, ethyl methacrylate, isobutyl methacrylate, isobutyl acrylate, hexyl methacrylate, 2-ethyl hexyl methacrylate, octyl methacrylate, cyclohexyl methacrylate, tetrahydrofurfuryl methacrylate, ethoxyethyl acrylate, methoxyethyl acrylate, tertiary butyl acrylate, isobornyl acrylate, isobornyl methacrylate, styrene, α-methyl styrene, vinyl versatate, vinyl acetate and vinyl propionate. A mixture of the aforementioned monomers may also be used. The optimal amount of monomer ii is about 29 to 45 percent by weight of the polymer composition, and is preferably about 33 percent, but may range from 15 to 80 percent.

For monomer iii, other suitable monomers which may be used instead of DMAEMA include t-butylaminoethyl methacrylate, acrylamide, methacrylamide, acrylic acid, methacrylic acid, maleic anhydride, fumaric acid, vinyl sulfonic acid, 2-acrylamidomethylpropane sulfonic acid, dimethylaminoethyl acrylate, diethylaminoethyl acrylate, 2-vinyl pyridine and 4-vinyl pyridine. The preferred amount of monomer iii is about 1 to 5 percent by weight of the polymer composition, but may range from 0 to 10 percent.

In a preferred embodiment, a solvent composition is used comprising two organic solvents, polar 1-methoxy-2-propanol and nonpolar xylene, in preferably equal amounts by weight. Other suitable solvents may also be used, and these include, as a substitute for methoxy propanol, butyl acetate, ethyl acetate, ethylene glycol diacetate, anisole, 1-4 dioxane, methyl isobutyl ketone, tetrahydrofuran and butyl acetate. Solvents which may be used instead of xylene include toluene, VM&P naphtha and higher aliphatic solvents.

The specific mechanism by which the novel copolymer film composition stabilizes enzymes is uncertain; however it is believed that the highly hydroxylated polymer coils surround and compress the enzymes producing steric stabilization. Furthermore, the hydrophilic nature of the polymer allows intimate and close contact with the serum, which produces rapid reaction when glucose is present. The polymer thus protects the flavin adenine dinucleotide (FAD) catalytic centers of the enzyme while allowing quick access to glucose molecules.

EXAMPLE 1

Preparation of Polymer

Following is a general free radical polymerization procedure used in the synthesis of a preferred polymer.

| Composition of Polymer 12D: | | |
|---|---|---|
| | Wt. g | Wt. % |
| Monomer: | | |
| HEMA[1] | 130 | 65 |
| BMA[2] | 66 | 33 |
| DMAEMA[3] | 4 | 2 |
| Initiator: | | |
| AIBN[4] | 2 | |
| Solvents: | | |
| Xylene | 150 | |
| 1-M-2-P[5] | 150 | |

[1]Hydroxyethyl methacrylate
[2]Butyl methacrylate
[3]Dimethylaminoethyl methacrylate
[4]2,2'-Azobis-2-methyl-propionitrile
[5]1-Methoxy-2-propanol The initiator was dissolved in the mixture of monomers at room temperature. The solvent mixture was kept at 90°±5° C. in a 3-necked flask. A mixture of monomers containing initiator was added dropwise to the solvent mixture at the rate of 150–200 g/h. The temperature was maintained and the system was under a nitrogen blanket. Polymerization was monitored and samples were taken periodically for solid content determination using a vacuum oven. Upon complete (100%) conversion of monomers to polymer, in this case reaching a 40% solids content, the polymer solution was cooled to room temperature and was ready for use. Cross-linking did not occur in preferred polymers prepared according to the teachings of the present invention because hydroxyethyl methacrylate of extremely low diacrylate content was used in preparation of the polymers.

EXAMPLES 2-12

Other preferred polymers were also prepared according to the above general procedure using the following monomers, weight ratios and initiators:

| Polymer | Monomers | Ratio | Initiator | Wt. g |
|---|---|---|---|---|
| 5 | HEMA/BMA/AA[1] | 65/34/1 | Bz$_2$O$_2$[2] | 2.0 |
| 5A | HEMA/BMA/AA | 64.36/33.66/1.98 | Bz$_2$O$_2$ | 2.5 |
| 6 | HPMA[3]/BMA/MMA[4] | 70/15/15 | Bz$_2$O$_2$ | 2.0 |
| 13 | HPMA/BMA/DMAEMA | 65/34/1 | Bz$_2$O$_2$ | 2.0 |
| 16 | HPMA/MMA/HEMA | 65/15/20 | Bz$_2$O$_2$ | 2.0 |
| 18 | HEMA/BMA | 65/35 | Bz$_2$O$_2$ | 2.0 |
| 22 | HEMA/BMA/PPGMM[5] | 65/34/1 | Bz$_2$O$_2$ | 2.0 |
| 23 | HEMA/BMA/HEM-10[6] | 65/34/1 | Bz$_2$O$_2$ | 2.0 |
| 24 | HEMA//BMA/GAE[7] | 65/34/1 | Bz$_2$O$_2$ | 2.0 |
| 30A | HEMA/BMA/T-BAEMA[8] | 65/34/1 | AIBN | 1.0 |
| 31 | HEMA/MMA/BMA/DMAEMA | 33/33/32/2 | AIBN | 1.0 |

[1]Acrylic acid
[2]Benzoyl peroxide
[3]Hydroxypropyl methacrylate
[4]Methyl methacrylate
[5]Polypropylene glycol monomethacrylate
[6]Polyethylglycol acrylate
[7]Glycidyl allyl ether
[8]t-Butylaminoethyl methacrylate
The solvents used in examples 2-12 were xylene and 1-M-2-P in equal weight amounts. A preferable weight ratio of solvents/monomers was 60/40.

EXAMPLE 13

Enzyme Dispersion

To obtain a fine homogeneous dispersion of coating mass and a smooth film surface, the particulate components were ground by using an Attritor mill (Union Process, Inc., Akron, Oh.). During attrition, particle size was substantially reduced by both impact action (constant impinging of the grinding media due to its irregular movement) and shearing force (random spinning of media in different rotations) on the adjacent slurry. To ensure minimal contamination of the sample in the presence of organic solvents, the grinding tank was Tefzel (registered trademark of E. I. DuPont deNemours Co., Inc.) coated and the agitator shaft and arm were plastic coated. Zirconium oxide grinding media (MgO stabilized) was used.

Particulate components, namely glucose oxidase (GOD), horseradish peroxidase (POD) and sodium dodecyl sulfate (SDS), were mixed with xylene and 1-M-2-P and dispersed in the Attritor mill for 2–4 hours. Dispersion temperature was kept low by circulating tap water in the jacket of the grinding tank. Dispersion was checked microscopically for uniformity and particle size. Using the procedure of this invention, dispersions of about 1 μm were obtained. Upon the completion of dispersion, media was strained from the product. The enzyme-SDS dispersion was kept at 4° C. until used. The composition of a typical enzyme-SDS dispersion is given below.

| Composition of a Preferred Enzyme-SDS Dispersion: | |
| --- | --- |
| Glucose oxidase | 1.876 g |
| Horseradish peroxidase | 4.298 g |
| Sodium dodecyl sulfate | 11.70 g |
| Xylene | 41.06 g |
| 1-M-2-P | 41.06 g |

An alternate and preferred method for preparation of enzyme dispersions employed a jar mill with ceramic beads as the grinding media. It was found to be desirable, also, to freeze dry the enzymes, SDS or Marlon, and TMB prior to use to remove any traces of moisture from the raw material, and to take precautions to keep the solvents (xylene and 1-M-2-P) moisture free. The enzyme dispersion could also be prepared using, e.g., a ball mill, shot mill, paint mill or sand mill.

EXAMPLES 14–15

Film Preparation

A coating mass consisting of the binder (polymer solution), enzyme-SDS dispersion and TMB was mixed in a glass container at room temperature until the TMB was completely dissolved. Some grinding media was used to facilitate the mixing on the jar mill. Additional liquid surfactants and other modifiers (see below) were added to the mass before coating. The mass was coated on polycarbonate using a hand rakel mounted on a coating line with a blade gap of 100μ at 2 m/min. The coating was dried in a forced air oven at 50°±2° C. for 15 minutes. Alternatively, other known coating method could also be used with the film compositions of the present invention such as spraying, spin coating and ink jet methods.

| Composition of Preferred Coating I: | |
| --- | --- |
| Polymer 12D | 42.0 g |
| TMB | 3.0 g |
| Enzyme-SDS dispersion: | 55.0 g |
| GOD | 1.03 g |
| POD | 2.36 g |
| SDS | 6.43 g |
| Xylene | 22.55 g |
| 1-M-2-P | 22.55 g |
| Igepal C-530 | 2.50 g |
| Silane Z6040 | 0.82 g |
| Klucel[1] | 1.15 g |
| Composition of Preferred Coating II: | |
| Polymer 30A | 44.8 g |
| TMB | 3.2 g |
| Enzyme-SDS dispersion: | 52.0 g |
| GOD | 0.97 g |
| POD | 2.23 g |
| SDS | 6.08 g |
| Xylene | 21.32 g |
| 1-M-2-P | 21.32 g |
| Igepal C-530 | 2.00 g |
| Silane Z6040 | 0.66 g |
| Klucel[1] | 0.92 g |

[1] 2% solution in 1-M-2-P

Modifiers used in the examples described herein were chosen for purposes that will be known to those skilled in the art. Sodium dodecyl sulfate (SDS) and alternatively, Marlon AS3 (sodium dodecylbenzene sulfonate), are detergents and have been found to be especially desirable when used with the present invention for their stabilizing effects on the TMB charged complex. Igepal CO-530 (GAF Chemicals Corp.) is a nonionic surfactant which enhances color formation and aids in red blood cell removal in the capillary-type apparatus. Silane Z6040 is a silane surfactant with an epoxy group which reduces red blood cell retention on the film surface, and Klucel GF (hydroxypropyl cellulose) is a water soluble polymer which aids in serum uptake and increases color intensity. Surfactant types and amounts are determined according to the specific effects desired and can be screened conveniently in the laboratory using a gravity flow test such as that described below, followed by further testing of promising materials using blood samples and a capillary flow device of the type described herein.

EXAMPLE 16

Glucose Measurement

In screening polymers for those mixtures which may be desirable for further evaluation and study, a simple gravity flow test was found to be convenient in which a drop of an aqueous glucose solution was allowed to flow over a vertical film surface. Criteria used for selection included speed of flow, rate of color formation, and intensity and quality of color formed.

Quantitative detection of glucose in blood samples was accomplished by incorporating the film into an analytical test device of the type in which blood is allowed or caused to flow across the surface of the film, i.e., in a plane parallel to that of the plane of the film and in fluid contact therewith. The film was coated onto a support material, and then a sample of blood was applied to one edge of the film and allowed to flow across the surface, e.g., by capillary or other forces, after which the film was observed for color formation which is indicative of the presence of glucose.

Figure 2:
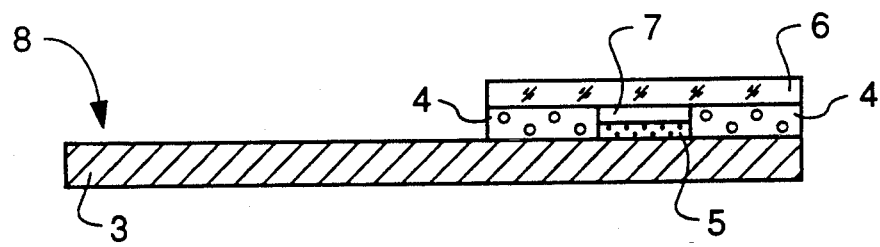
FIG. 2 is a sectional view through plane 2—2 of the embodiment shown in FIG. 1. It illustrates the support, reagent film, adhesive and cover piece which comprise the test apparatus.

More specifically, to construct a test apparatus as illustrated in FIG. 1 and FIG. 2, the preferred coating I was applied to an area near one end of a rectangular polycarbonate support piece 3 measuring 40 mm×10 mm, thereby forming the reaction pad 5. The area covered by the coating measured 5 mm×10 mm. On each of two opposing sides of the coated reaction pad, a strip of double-faced adhesive 4, 6 mm wide×10 mm long×0.2 mm thick, was applied to serve as a spacer and as a support for the covering piece of clear plastic 6 which was then applied thereon, thereby forming a channel 7 through which blood or other sample could flow, such as by capillary action. In testing the polymer film of the present invention, an especially convenient means for constructing numerous analytical test devices for performing a large number of glucose measurements was that in which the preferred coatings were applied to a sheet polycarbonate support material 40 mm in width by a length sufficient to produce the desired quantity of test pieces. Such material is often supplied in roll form. The film was then dried, adhesive strips and clear covering material were applied as described more fully below, and the assembly was cut crosswise into strips 10 mm in width for convenience in testing.

Figure 3:
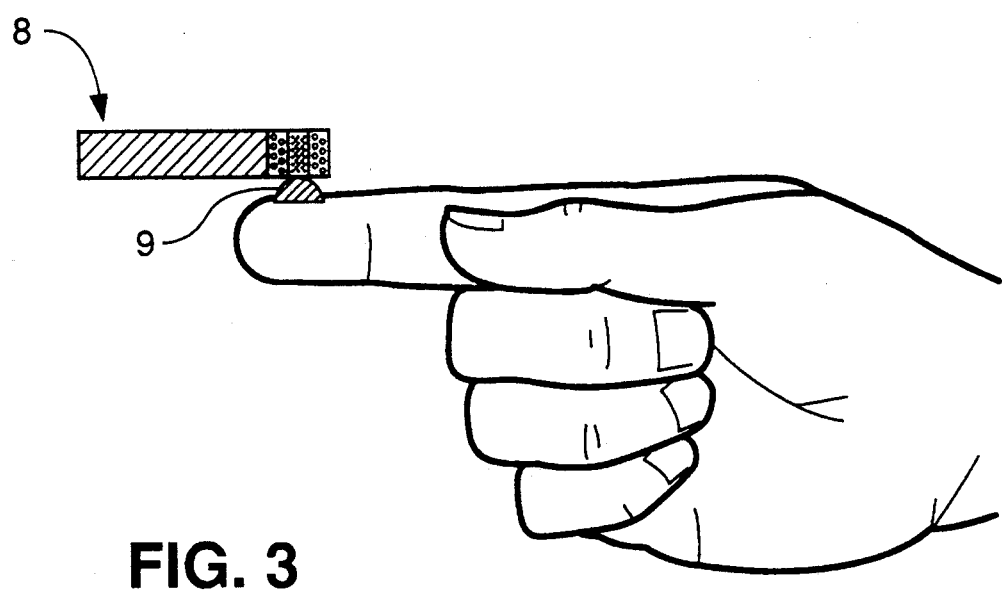
FIG. 3 illustrates a method for applying a sample to the apparatus of FIG. 1 whereby the edge of the apparatus is brought into contact with a drop of blood such as that obtained from a fingerstick.

As illustrated in FIG. 3, the sample was conveniently brought into contact with the reaction pad 5 and the channel 7 by grasping the handle end 8 of the test apparatus and touching one edge of the leading end of the apparatus to a drop of blood 9. After a suitable reaction interval, normally only a few seconds, the excess blood and cells were removed from the device by touching the edge opposite that to which the sample was applied to an absorbent material, e.g., paper, a piece of cotton or synthetic nonwoven material. Reflectance was then measured using a Macbeth visible spectrophotometer. Using such test devices of the present invention, blood glucose was detected over a wide range of glucose concentrations (about 30 to 600 mg/dl) with excellent resolution. Color development was found to be independent of blood residence time on the film, indicating a rapid end-point characteristic of the film of the instant invention.

EXAMPLES 17-18

For measurement of glucose levels in the higher range (about 240 to 800 mg/dl), in order to improve resolution, it was found that certain antioxidants, referred to herein as ranging compounds, could be added to the polymer coating mixture with no harmful effects to the assay, in marked contrast to other methods that employ aqueous polymer films, whereby a new added component can strongly interact with one or more film constituents. Polymer solutions were prepared which incorporated such ranging compounds, e.g., 3-amino-9-(-aminopropyl)-carbozol dihydrochloride (APAC), butylated hydroxytoluene (BHT), or propyl gallate (PG). These compounds partially consume the color signal that is formed and thus provide a greater change in percent reflectance at higher glucose levels, thereby permitting their measurement without dilution of the sample. Using polymer 12D, APAC was preferably included at an APAC:TMB molar ratio of about 1:20, and with polymer 30A, an optimal molar ratio of about 1:15 was found. Using polymer 12D, the ranging compound BHT was found to be optimally included at a 1:2.5 molar ratio of BHT:TMB. Using the preferred coating III, described below, and samples having glucose levels ranging between about 200 and 800 mg/dl, a range in percent reflectance of about 30 was observed, thus enhancing the dynamic range of the coating film.

Figure 4:
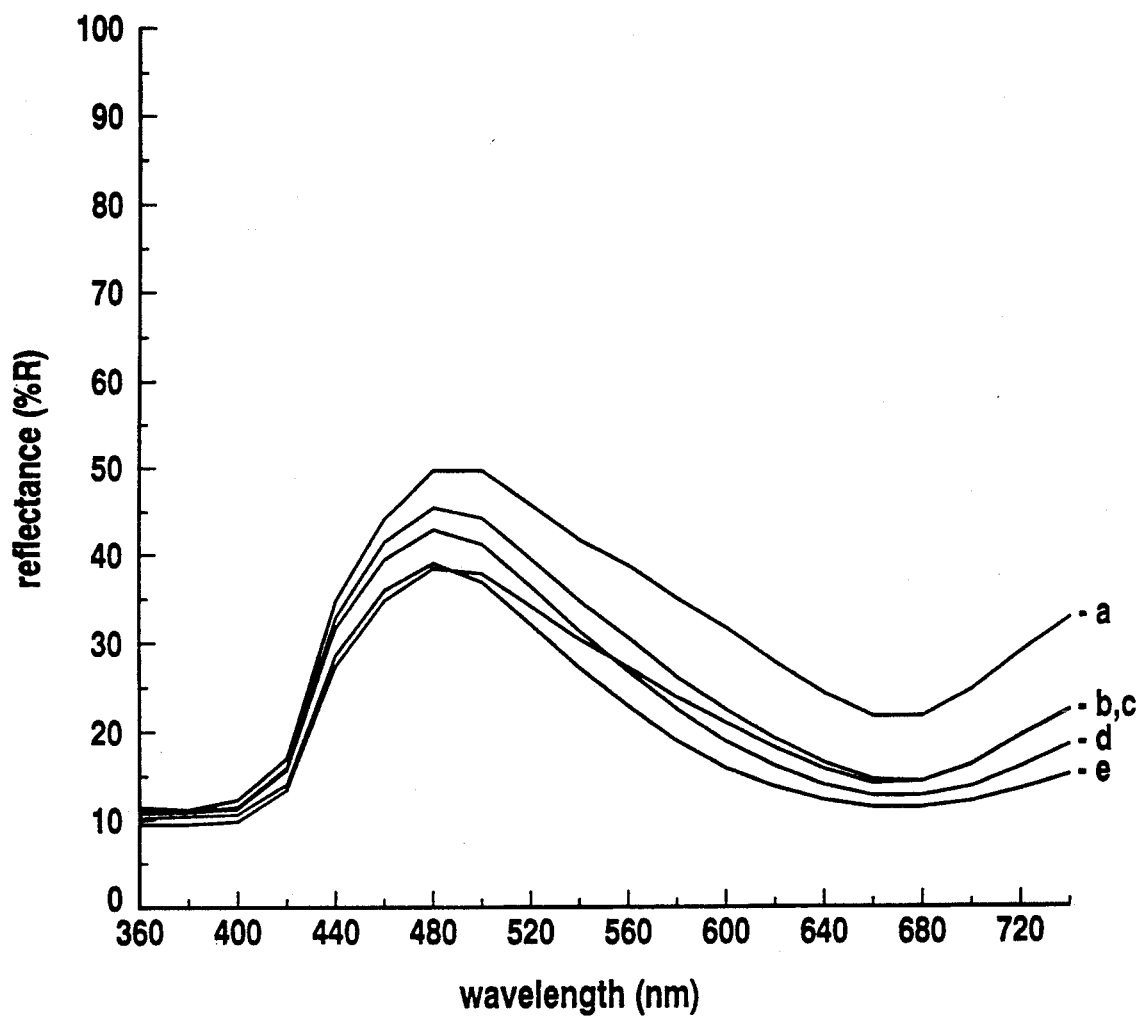
FIG. 4 illustrates the dose response curves obtained using polymer 12D and samples having glucose concentrations in the high range, specifically from 171 mg/dl through 786 mg/dl.
Figure 5:
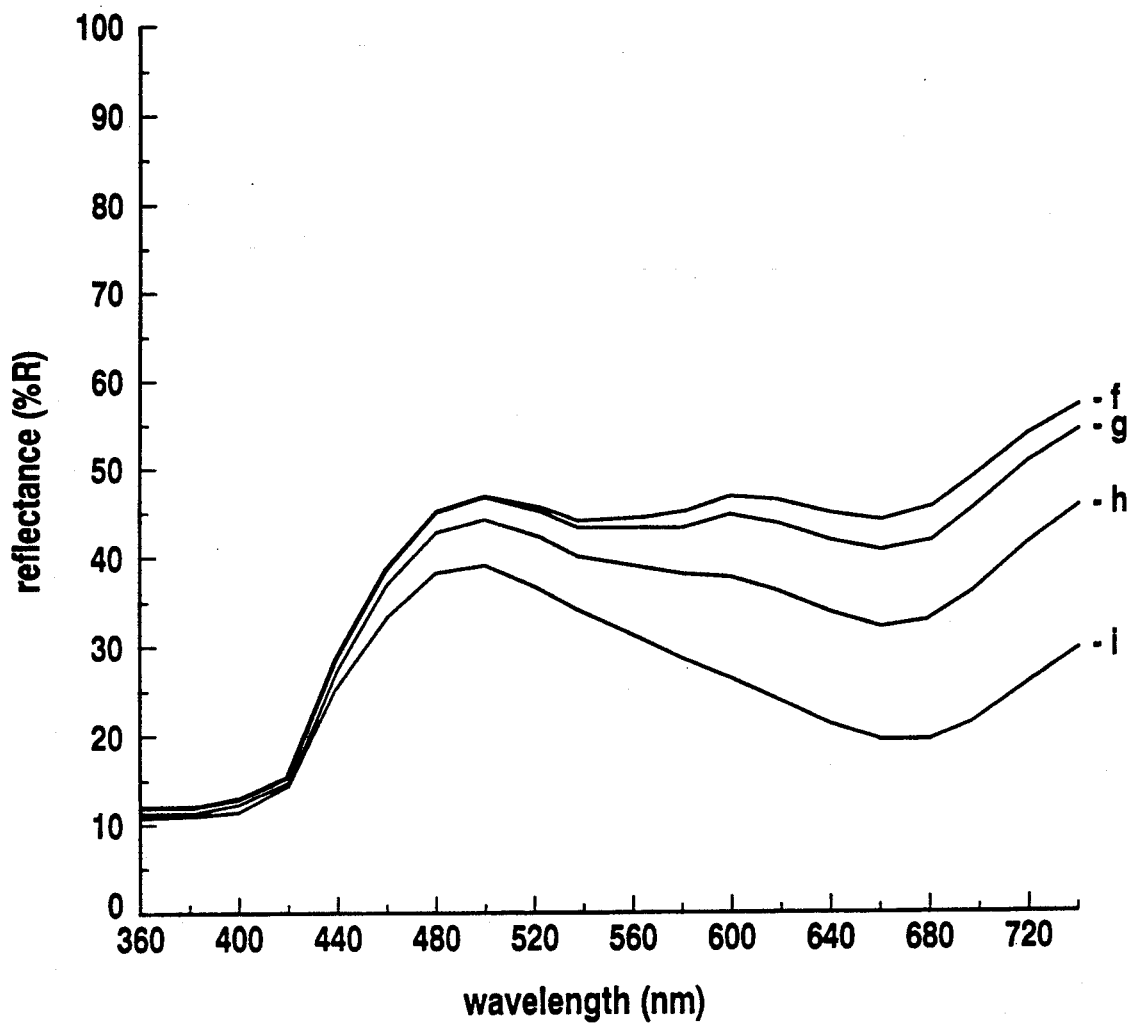
FIG. 5 illustrates the dose response curves obtained using a film composition containing polymer 12D and APAC ranging compound with samples having glucose concentrations ranging from 209 mg/dl to 788 mg/dl.

More specifically, FIG. 4 shows dose response curves for five samples ranging in glucose concentration from 171 mg/dl to 786 mg/dl. The coating mixture used was comprised of polymer 12D in the absence of a ranging compound. At 660 nm, curve a (171 mg/dl), curve b (282 mg/dl), curve c (344 mg/dl), curve d (507 mg/dl) and curve e (786 mg/dl) exhibit a total change in reflectance (%R) of about 10, thus precluding accurate measurement of glucose at these levels. On the other hand, FIG. 5 illustrates dose response curves at four glucose levels using a coating mixture that included both polymer 12D and APAC. At 660 nm, curve f (109 mg/dl), curve g (268 mg/dl), curve h (450 mg/dl) and curve i (788 mg/dl) exhibit a difference in reflectance of almost 30 units, or a three-fold improvement.

| Detection: | | |
|---|---|---|
| Composition of Preferred Coating III for High Range | | |
| Polymer 12D | 1.68 g | 32.13% |
| TMB | 0.12 g | 2.30 |
| GOD | 0.0589 g | 1.13 |
| POD | 0.1355 g | 2.59 |
| SDS | 0.276 g | 5.28 |
| Solvents | 2.678 g | 51.22 |
| Mica | 0.099 g | 1.89 |
| Flowtone 4 | 0.148 g | 2.83 |
| APAC (14.3%) | 0.033 g | 0.63 |
| Composition of Preferred Coating IV for High Range | | |
| Polymer 12D | 1.68 g | 33.29% |
| TMB | 0.12 g | 2.38 |
| GOD | 0.0589 g | 1.17 |
| POD | 0.1355 g | 2.68 |
| Marlon AS3 | 0.1656 g | 3.28 |
| Solvents | 2.678 g | 53.06 |
| Mica | 0.099 g | 1.96 |
| BHT | 0.11 g | 2.18 |

Flowtone 4, an optional viscosity modifying agent, is a sulfonated castor oil which was incorporated to improve viscosity, sag and leveling control, pigment suspension and color uniformity. Flowtone 4 at levels of 3% and 6% produced films with smooth surfaces, good flow properties, improved color uniformity and low red blood cell retention.

Several formulations exhibited moderate to high levels of tack, which was observed upon rewinding of the coated material as the film surface stuck to the back side of the polycarbonate substrate. Thus, e.g. in preferred coating III, ground Muscovite mica (micro mica C-4000) was incorporated up to 6% by weight of the formulation and mixed well before coating. It was found that 2% mica in the formulation was effective to prevent film tack under the coating and drying conditions used. Addition of mica up to 6% weight of the formulation did not affect the coating and no deleterious effects on red cell retention or blood flow properties were observed. Mica can, therefore, be used as an inert substance to increase solids content of the formulation, affecting mixing, settling, particle size distribution and other properties of the coating mass.

EXAMPLES 19-21

Additional preferred coating compositions were made using polymer 12D, and dose response curves were prepared using these formulations which were designed for low range detection (coating V) and for high range detection (coating IV). In coating VI, a mixture of the BHT and PG ranging compounds was used. Also in coating VI, a non-functional dye, Golden Yellow, was incorporated for cosmetic purposes.

Preferred coating VII was specially formulated with a higher solids content to improve film flow characteristics, which was found to be preferred for manufacturing test devices in larger quantities. Specifically, coating VII had a solids content of 42.3% compared with a solids content of 25.7% for coatings V and VI.

Figure 6:
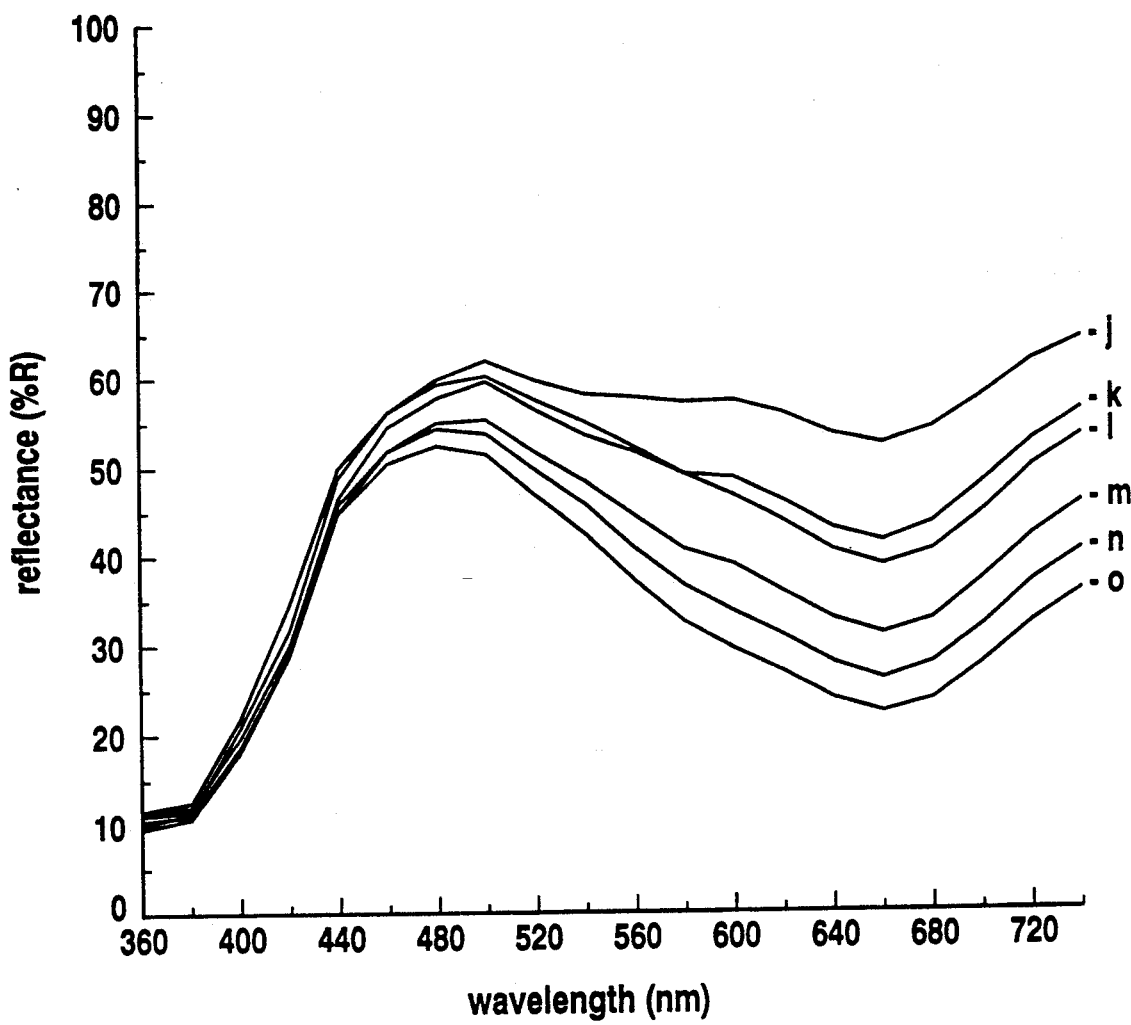
FIG. 6 illustrates the dose response curves obtained using a preferred film composition containing polymer 12D and no ranging compound with blood samples having glucose concentrations ranging from 30 mg/dl to 231 mg/dl.

FIG. 6 shows dose response curves for six samples ranging in glucose concentration from 30 mg/dl to 231 mg/dl. The coating mixture used was comprised of polymer 12D in the absence of a ranging compound. At 660 nm, curve j (30 mg/dl), curve k (55 mg/dl), curve l (84 mg/dl), curve m (127 mg/dl), curve n (175 mg/dl) and curve o (231 mg/dl) exhibit a total change in reflectance (%R) of over 30, thus allowing for accurate measurement of glucose at these levels.

Figure 7:
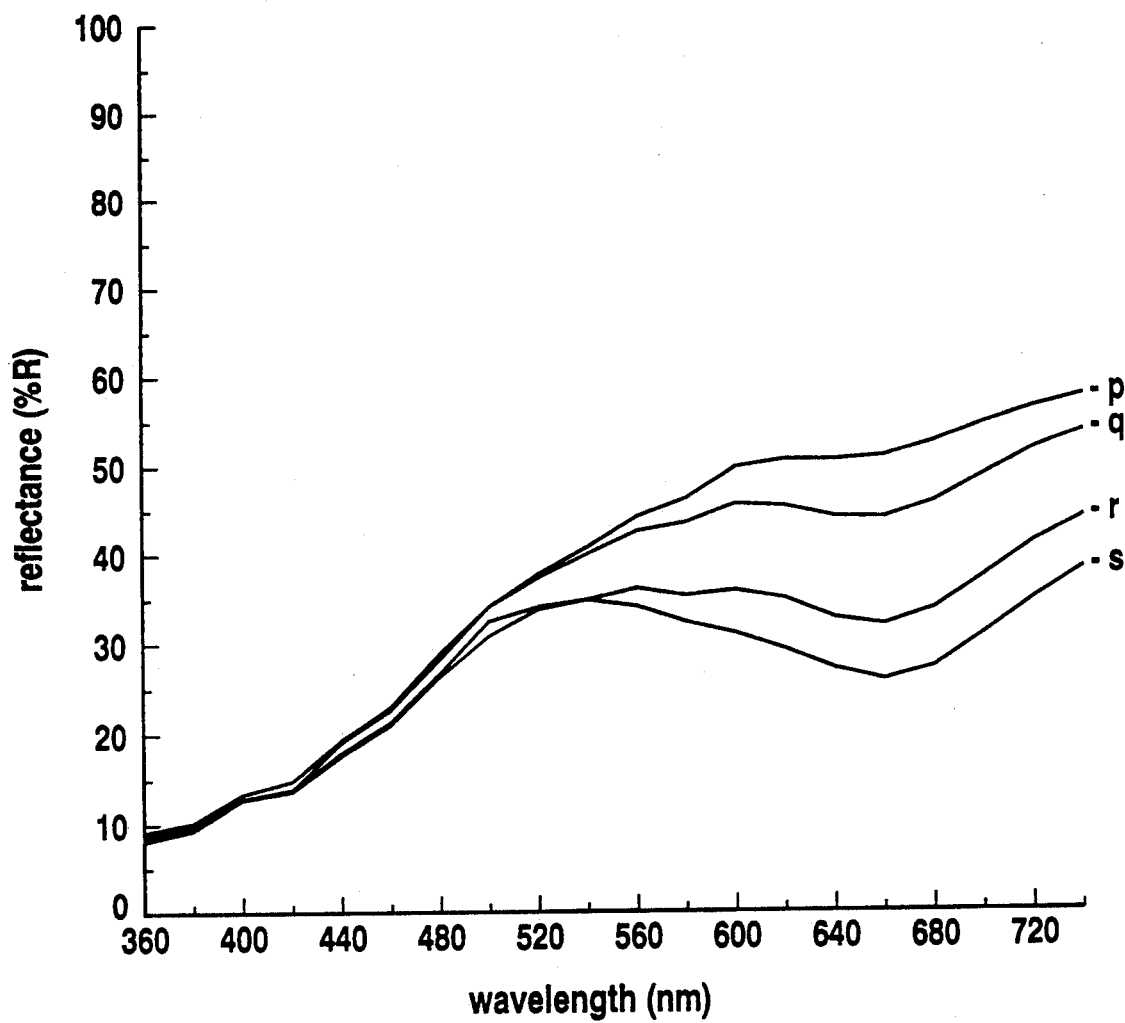
FIG. 7 illustrates the dose response curves obtained using a preferred film composition containing polymer 12D plus BHT and PG ranging compounds with blood samples having glucose concentrations ranging from 172 mg/dl to 557 mg/dl.

FIG. 7 illustrates dose response curves at four glucose levels using a coating mixture that included both polymer 12D and the ranging compounds BHT and PG. At 660 nm, curve p (172 mg/dl), curve q (246 mg/dl), curve r (450 mg/dl) and curve s (557 mg/dl) exhibit a difference in reflectance of almost 30 units, again providing for accurate glucose measurement over the range of values tested.

Figure 8:
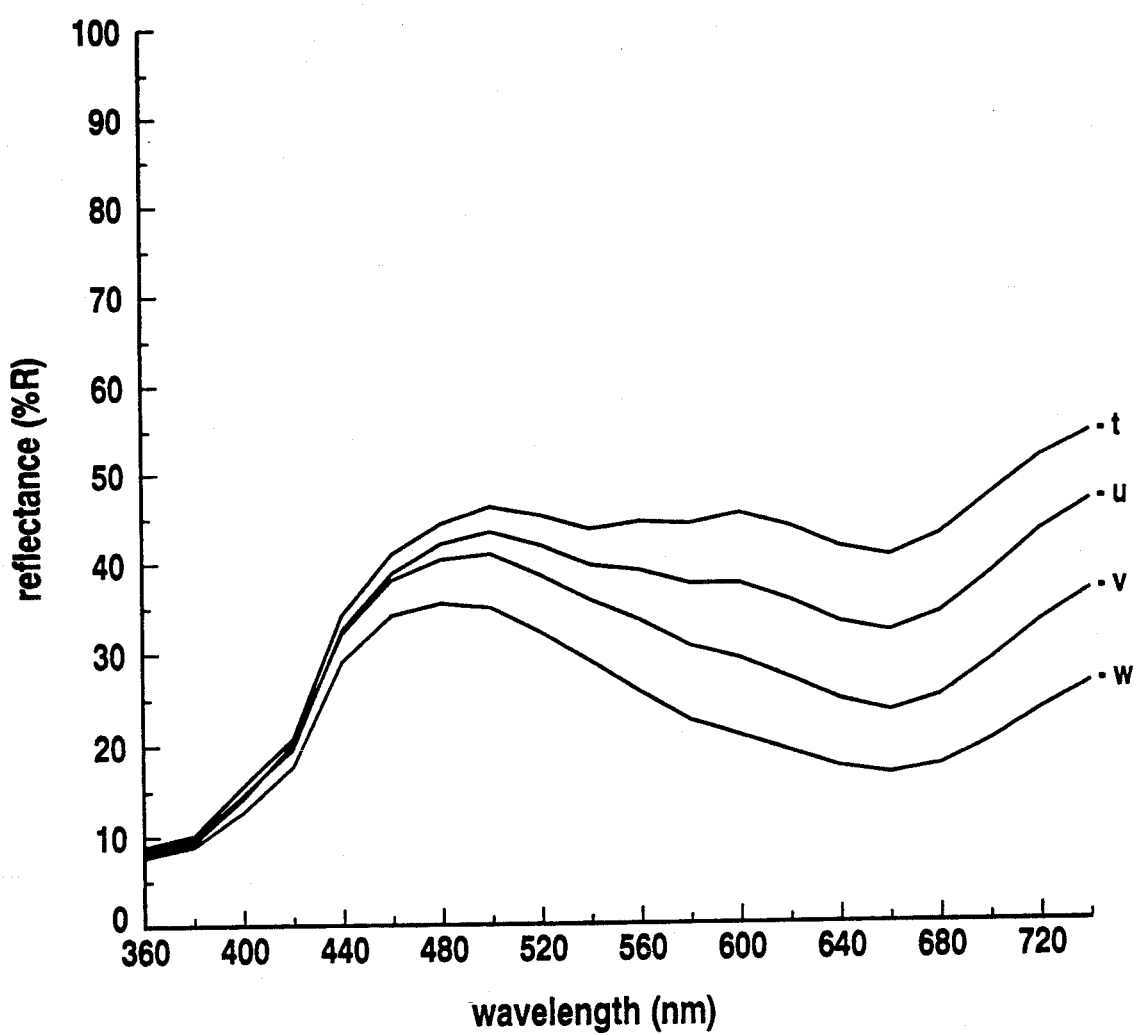
FIG. 8 illustrates the dose response curves obtained using a preferred film composition containing polymer 12D, BHT and PG ranging compounds, and a high percentage solids content with blood samples having glucose concentrations ranging from 196 mg/dl to 600 mg/dl.
Figure 9:
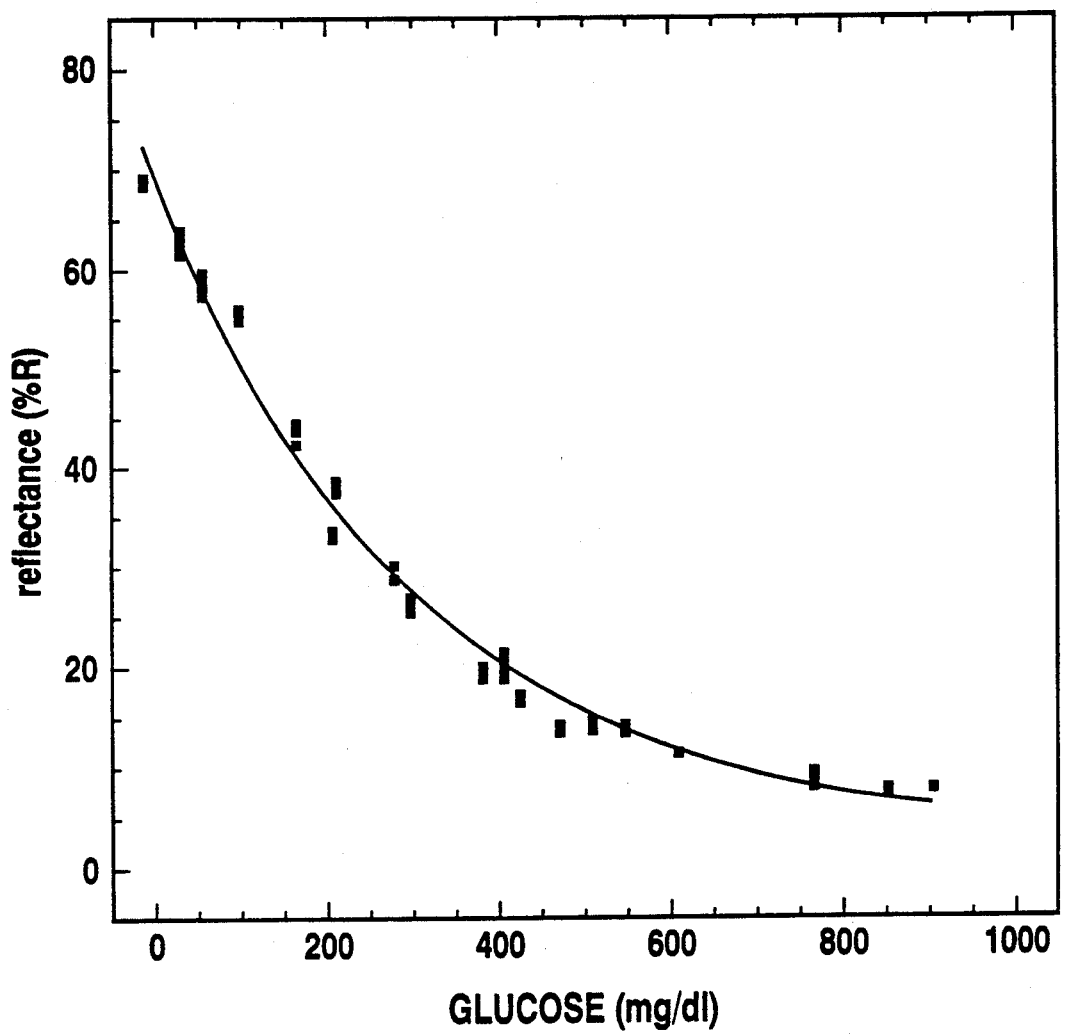
FIG. 9 illustrates a linear regression curve obtained comparing actual versus theoretical whole blood glucose concentrations using a preferred film composition containing polymer 12D, BHT and PG ranging compounds, and a high percentage solids content. The blood samples had glucose concentrations ranging between about 5 mg/dl and 900 mg/dl.

FIG. 8 illustrates dose response curves at four glucose levels using a coating mixture that included both polymer 12D, the ranging compounds BHT and PG, and which was formulated with a high solids content. At 660 nm, curve t (196 mg/dl), curve u (280 mg/dl), curve v (420 mg/dl) and curve w (600 mg/dl) exhibit a difference in reflectance of almost 30 units.

| Composition of Preferred Coating V for Low Range Detection: | | |
|---|---|---|
| Polymer 12D | 1.68 g | 33.29% |
| TMB | 0.12 g | 2.38 |
| GOD | 0.0589 g | 1.17 |
| POD | 0.1355 g | 2.68 |
| Marlon AS3 | 0.1656 g | 3.28 |
| Solvents | 2.678 g | 53.06 |
| Mica | 0.099 g | 1.96 |
| Composition of Preferred Coating VI for High Range Detection: | | |
| Polymer 12D | 1.68 g | 33.29% |
| TMB | 0.12 g | 2.38 |
| GOD | 0.0589 g | 1.17 |
| POD | 0.1355 g | 2.68 |
| Marlon AS3 | 0.1656 g | 3.28 |
| Solvents | 2.678 g | 53.06 |
| Mica | 0.099 g | 1.96 |
| BHT | 12 mg | |
| PG | 1.6 mg | |
| Golden Yellow dye | 25 mg | |
| Composition of Preferred Coating VII with Increased Solids for High Range Detection: | | |
| Polymer 12D | 1.68 g | 33.29% |
| TMB | 0.12 g | 2.38 |
| GOD | 0.0589 g | 1.17 |
| POD | 0.1355 g | 2.68 |
| Marlon AS3 | 0.1656 g | 3.28 |
| Solvents | 2.678 g | 53.06 |
| Mica | 0.099 g | 1.96 |
| BHT | 86.5 mg | |
| PG | 15.6 mg | |

EXAMPLE 22

The film compositions of the present invention may also be conveniently buffered in order to impart special conditions required for a particular purpose, for example, to adjust pH in order to reduce a chemical interference. Uric acid in blood samples at a level of 30 mg/dl was found to significantly decrease the color intensity at glucose levels below 180 mg/dl, resulting in a bleaching effect. Color development at higher glucose levels was not affected by the presence of uric acid. Thus, it was desired to lower the surface pH of the polymer film from 7.0 to below 6, where uric acid effects were expected to be minimal or completely eliminated. 2-(N-Morpholino)ethanesulfonic acid (MES) buffer at 6 mmol/g coating mass lowered the film pH to 5.5 and completely eliminated the interference of uric acid added to whole blood samples up to 30 mg/dl.

It will be understood that the specification and examples are illustrative but not limitative of the present invention and that other embodiments within the spirit and scope of the invention will suggest themselves to those skilled in the art.

What is claimed is:

1. A hydrophilic reagent composition for determining an analyte in a sample comprising:
   (a) a nonaqueous copolymer formed from a mixture comprising:
      (i) a first monomer of the general formula

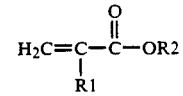

where R1 is hydrogen or methyl, and R2 is a hydroxyalkyl group having from 1 to 5 carbon atoms,
      (ii) a second monomer of the general formula

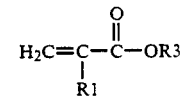

where R1 is hydrogen or methyl and R3 is a substituted or unsubstituted alkyl group having from 1 to 8 carbon atoms and wherein said second monomer is neutral in charge,
      (iii) an organic solvent, and
      (iv) an initiator in an amount sufficient for causing polymerization of the monomers;
   (b) an enzyme in powder form homogeneously dispersed in said copolymer and reactive with said analyte; and
   (c) an indicator in an amount sufficient to generate a detectable signal when in the presence of said analyte and said enzyme.

2. The composition of claim 1, wherein said copolymer is formed from a mixture further comprising a third monomer of the formula

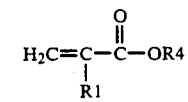

where R1 is hydrogen or methyl and R4 is hydrogen, an aminoalkyl or glycidyl group having from 1 to 5 carbon atoms or a surfactant polyethylene glycol group having from 10 to 30 carbon atoms, and wherein said third monomer is present in an amount less than about 5 percent by weight of the copolymer composition.

3. The composition of claim 1 or 2 wherein said first monomer is present in an amount of at least about 33 percent by weight of the copolymer composition.

4. The composition of claim 1 or 2 wherein said first monomer is present in an amount greater than about 50 percent by weight of the copolymer composition.

5. The composition of claim 1 or 2 wherein said first monomer is selected from the group consisting of hydroxyethyl methacrylate and hydroxypropyl methacrylate.

6. The composition of claim 1 or 2 wherein said second monomer is selected from the group consisting of butyl methacrylate and methyl methacrylate.

7. The composition of claim 2 wherein said third monomer is selected from the group consisting of dimethylaminoethyl methacrylate and t-butylaminoethyl methacrylate.

8. The composition of claim 1 or 2 wherein said organic solvent is comprised of a mixture of xylene and 1-methoxy-2-propanol.

9. The composition of claim 1 or 2 wherein said copolymer is nonionic.

10. The composition of claim 1 or 2 wherein said enzyme is selected from the group consisting of glucose oxidase and a peroxidase.

11. The composition of claim 1 or 2 wherein said indicator is selected from the group consisting of 3,3',5,5'-tetramethylbenzidine, a derivative thereof and an analog thereof.

12. The composition of claim 1 or 2, further comprising a ranging compound selected from the group consisting of 3-amino-9-(-aminopropyl)-carbozol dihydrochloride and butylated hydroxytoluene, wherein said ranging compound is present in an amount sufficient to reduce signal generation by said indicator, thereby making said composition useful for determining high levels of said analyte.

13. The composition of claim 1 or 2, further comprising a detergent selected from the group consisting of sodium dodecyl sulfate and sodium dodecylbenzene sulfonate.

14. The composition of claim 1 or 2, further comprising ground micro mica in an amount sufficient to reduce film tack.

15. An apparatus for determining an analyte in a sample comprising a carrier which is inert with respect to said analyte and a hydrophilic reagent composition coated thereon, said reagent composition comprising:
(a) a nonaqueous copolymer formed from a mixture comprising:
(i) a first monomer of the formula

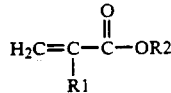

where R1 is hydrogen and methyl, and R2 is a hydroxyalkyl group having from 1 to 5 carbon atoms,
(ii) a second monomer of the formula

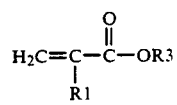

where R1 is hydrogen or methyl and R3 is a substituted or unsubstituted alkyl group having from 1 to 8 carbon atoms and wherein said second monomer is neutral in charge,
(iii) an organic solvent, and
(iv) an initiator in an amount sufficient for causing polymerization of the monomers;
(b) an enzyme in powder form homogeneously dispersed in said copolymer and reactive with said analyte; and
(c) an indicator in an amount sufficient to generate a detectable signal when in the presence of said analyte and said enzyme.

16. The apparatus of claim 15, wherein said copolymer is formed from a mixture further comprising a third monomer of the formula

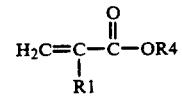

where R1 is hydrogen and methyl and R4 is hydrogen, an aminoalkyl or glycidyl group having from 1 to 5 carbon atoms or a surfactant polyethylene glycol group having from 10 to 30 carbon atoms, and wherein said third monomer is selected from the group consisting of present in an amount less than about 5 percent by weight of the copolymer composition.

17. The apparatus of claim 15 or 16 wherein said first monomer is present in an amount of at least about 33 percent by weight of the copolymer composition.

18. The apparatus of claim 15 or 16 wherein said first monomer is present in an amount from about 10 to 70 percent by weight of the copolymer composition.

19. The apparatus of claim 15 or 16 wherein said first monomer is selected from the group consisting of hydroxyethyl methacrylate and hydroxypropyl methacrylate.

20. The apparatus of claim 15 or 16 wherein said second monomer is selected from the group consisting of butyl methacrylate and methyl methacrylate.

21. The apparatus of claim 16 wherein said third monomer is selected from the group consisting of dimethylaminoethyl methacrylate and t-butylaminoethyl methacrylate.

22. The apparatus of claim 15 or 16 wherein said organic solvent is comprised of a mixture of xylene and 1-methoxy-2-propanol.

23. The apparatus of claim 15 or 16 wherein said copolymer is nonionic.

24. The apparatus of claim 15 or 16 wherein said enzyme is selected from the group consisting of glucose oxidase and a peroxidase.

25. The apparatus of claim 15 or 16 wherein said indicator is selected from the group consisting of 3,3',5,5'-tetramethylbenzidine, a derivative thereof and an analog thereof.

26. The apparatus of claim 15 or 16, wherein said reagent composition further comprises a ranging compound selected from the group consisting of 3-amino-9-(-aminopropyl)-carbozol dihydrochloride and butylated hydroxytoluene, wherein said ranging compound is present in an amount sufficient to reduce signal generation by said indicator, thereby making said composition useful for determining high levels of said analyte.

27. The apparatus of claim 15 or 16, wherein said reagent composition further comprises a detergent selected from the group consisting of sodium dodecyl sulfate and sodium dodecylbenzene sulfonate.

28. The apparatus of claim 15 or 16, wherein said reagent composition further comprises ground micro mica in an amount sufficient to reduce film tack.

29. A method for determining an analyte in a sample by contacting said sample with a hydrophilic reagent composition to form a reaction mixture and observing said reaction mixture for the appearance of a detectable signal, wherein said reagent composition comprises:
(a) a nonaqueous copolymer formed from a mixture of:
(i) a first monomer of the formula

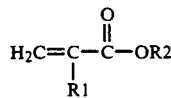

where R1 is hydrogen or methyl, and R2 is a hydroxyalkyl group having from 1 to 5 carbon atoms,
(ii) a second monomer of the formula

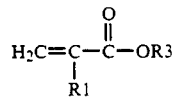

where R1 is hydrogen and methyl and R3 is a substituted or unsubstituted alkyl group having from 1 to 8 carbon atoms and wherein said second monomer is neutral in charge,
(iii) an organic solvent, and
(iv) an initiator in an amount sufficient for causing polymerization of the monomers;
(b) an enzyme in powder form homogeneously dispersed in said copolymer and reactive with said analyte; and
(c) an indicator in an amount sufficient to generate said detectable signal when in the presence of said analyte and said enzyme.

30. The method of claim 29, wherein said copolymer is formed from a mixture further comprises a third monomer of the general formula

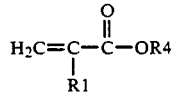

where R1 is hydrogen and methyl and R4 is hydrogen, an aminoalkyl or glycidyl group having from 1 to 5 carbon atoms or a surfactant polyethylene glycol group having from 10 to 30 carbon atoms, and wherein said third monomer is selected from the group consisting of present in an amount less than about 5 percent by weight of the copolymer composition.

31. The method of claim 29 or 30 wherein said first monomer is present in an amount of at least about 33 percent by weight of the copolymer composition.

32. The method of claim 29 or 30 wherein said first monomer is from about 10 to 70 percent by weight of the copolymer composition.

33. The method of claim 29 or 30 wherein said first monomer is selected from the group consisting of hydroxyethyl methacrylate and hydroxypropyl methacrylate.

34. The method of claim 29 or 30 wherein said second monomer is selected from the group consisting of butyl methacrylate and methyl methacrylate.

35. The method of claim 30 wherein said third monomer is selected from the group consisting of dimethylaminoethyl methacrylate and t-butylaminoethyl methacrylate.

36. The method of claim 29 or 30 wherein said organic solvent is comprised of a mixture of xylene and 1-methoxy-2-propanol.

37. The method of claim 29 or 30 wherein said copolymer is nonionic.

38. The method of claim 29 or 30 wherein said enzyme is selected from the group consisting of glucose oxidase or a peroxidase.

39. The method of claim 29 or 30 wherein said indicator is selected from the group consisting of 3,3',5,5'-tetramethylbenzidine, a derivative thereof and an analog thereof.

40. The method of claim 29 or 30, wherein said reagent composition further comprises a ranging compound selected from the group consisting of 3-amino-9-(-aminopropyl)-carbozol dihydrochloride and butylated hydroxytoluene, wherein said ranging compound is present in an amount sufficient to reduce signal generation by said indicator, thereby making said composition useful for determining high levels of said analyte.

41. The method of claim 29 or 30, wherein said reagent composition further comprises a detergent selected from the group consisting of sodium dodecyl sulfate and sodium dodecylbenzene sulfonate.

42. The method of claim 29 or 30, wherein said reagent composition further comprises ground micro mica in an amount sufficient to reduce film tack.

* * * * *